(12) United States Patent
Vind et al.

(10) Patent No.: US 9,163,203 B2
(45) Date of Patent: Oct. 20, 2015

(54) LIPOLYTIC ENZYME VARIANT WITH IMPROVED STABILITY AND POLYNUCLEOTIDES ENCODING SAME

(75) Inventors: Jesper Vind, Vaerloese (DK); Kim Borch, Birkeroed (DK); Allan Svendsen, Hoersholm (DK); Robert Van der Lans, Valby (DK); Lise Munch Mikkelsen, Roedeovre (DK); Christian Isak Jorgensen, Bagsvaerd (DK); Shamkant Anant Patkar, Lyngby (DK)

(73) Assignee: NOVOZYMES A/S, Bagsvaerd (DK)

( * ) Notice: Subject to any disclaimer, the term of this patent is extended or adjusted under 35 U.S.C. 154(b) by 152 days.

(21) Appl. No.: 12/393,512

(22) Filed: Feb. 26, 2009

(65) Prior Publication Data

US 2009/0221034 A1    Sep. 3, 2009

Related U.S. Application Data

(60) Provisional application No. 61/033,097, filed on Mar. 3, 2008.

(30) Foreign Application Priority Data

Feb. 29, 2008    (EP) .................................... 08152164

(51) Int. Cl.
*C12N 9/20* (2006.01)
*C11D 3/386* (2006.01)
*C12N 15/00* (2006.01)
*C07H 21/04* (2006.01)

(52) U.S. Cl.
CPC .............. *C11D 3/38627* (2013.01); *C12N 9/20* (2013.01); *C12N 15/00* (2013.01)

(58) Field of Classification Search
CPC .......... C12N 9/20; C12N 15/00; C12D 3/386; C12D 3/38627
See application file for complete search history.

(56) References Cited

U.S. PATENT DOCUMENTS

| | | | |
|---|---|---|---|
| 5,176,796 A | 1/1993 | Irie et al. | |
| 5,892,013 A | 4/1999 | Svendsen et al. | |
| 7,157,263 B2 * | 1/2007 | Munk et al. | 435/198 |
| 7,172,997 B2 * | 2/2007 | Minning et al. | 510/226 |
| 7,786,067 B2 * | 8/2010 | Souter et al. | 510/419 |
| 7,790,666 B2 * | 9/2010 | Souter et al. | 510/419 |
| 7,919,298 B2 * | 4/2011 | Vind et al. | 435/198 |
| 8,187,854 B2 * | 5/2012 | Vind et al. | 435/198 |
| 8,273,348 B2 * | 9/2012 | Svendsen et al. | 424/94.2 |
| 8,679,813 B2 * | 3/2014 | Vind et al. | 435/198 |
| 2006/0229223 A1 * | 10/2006 | Minning et al. | 510/320 |

FOREIGN PATENT DOCUMENTS

| | | |
|---|---|---|
| EP | 0 258 068 | 8/1994 |
| EP | 0 305 216 | 8/1995 |
| WO | WO 92/05249 | 4/1992 |
| WO | WO 92/13130 | 8/1992 |
| WO | WO 92/19726 | 11/1992 |
| WO | WO 97/07202 | 2/1997 |
| WO | WO 00/60063 | 10/2000 |
| WO | WO 02/055679 | 7/2002 |
| WO | WO 2006/084470 | 8/2006 |
| WO | WO 2007/087242 | 8/2007 |
| WO | WO 2007/087319 | 8/2007 |
| WO | WO 2008/079685 | 7/2008 |

OTHER PUBLICATIONS

Branden et al. Introduction to Protein Structure, Garland Publishing Inc., New York, p. 247, 1991.*
Rodriguez-Larrea et al, J. Mol. Biol. vol. 360, pp. 715-724 (2006).

* cited by examiner

*Primary Examiner* — Yong Pak
(74) *Attorney, Agent, or Firm* — Kristin J. McNamara

(57) ABSTRACT

The invention provides lipolytic enzyme variants having improved in-detergent stability and polynucleotides encoding same. Lipolytic enzyme variants with improved in-detergent stability are obtained by substituting certain specified amino acid residues in a parent lipolytic enzyme.

9 Claims, 3 Drawing Sheets

```
ID NO 1:    SSSSTQDYRIASEAEIKAHTFYTALSANA
ID NO 2:     SSSTQDYRIASEAEIKAHTFYTALSANA
ID NO 3:      SIDGGIRAATSQEINELTYYTTLSANS
ID NO 4:    SASDGGKVVAATTAQIQEFTKYAGIAATA
ID NO 5:        TAGHALAASTQ GISEDLYSRL VEMATISQAA
ID NO 6:        TAGHALAASTQ GISEDLYSRL VEMATISQAA
ID NO 7:            AVGVTTTDFSNFKFYIQHGAAA
ID NO 8:             TVTTQDLSNFRFYLQHADAA
ID NO 9:             DIPTTQLEDFKFWVQYAAAT
ID NO 10:            DVSTSELDQFEFWVQYAAAS
ID NO 11:            SVSTSTLDELQLFAQWSAAA
ID NO 12:            SVSTSTLDELQLFSQWSAAA
ID NO 13:            DVSSSLLNNLDLFAQYSAAA
ID NO 14:            EVSQDLFNQFNLFAQYSAAA
ID NO 15:          PQDAYTASHADLVKYATYAGLA

ID NO 1:    YCRTVIPG      GRWSCPHCGVAS  NLQITKTFST   LITDTNVLVAV
ID NO 2:    YCRTVIPG      GQWSCPHCDVAP  NLNITKTFTT   LITDTNVLVAV
ID NO 3:    YCRTVIPG      ATWDCIHCDATE  DLKIIKTWST   LIYDTNAMVAR
ID NO 4:    YCRSVVPG      NKWDCVQCQKWVP DGKIITTFTS   LLSDTNGYVLR
ID NO 5:    YADLCNIPST                  IIKGEKIYNSQTDINGWILR
ID NO 6:    YADLCNIPST                  IIKGEKIYNSQTDINGWILR
ID NO 7:    YC   NSEAAA GSKITCSNNGCPTVQGNGATIVTSF  VGSKTGIGGYVAT
ID NO 8:    YC   NFNTAV GKPVHCSAGNCPDIEKDAAIVVGSV  VGTKTGIGAYVAT
ID NO 9:    YCPNNYVAKD GEKLNCSVGNCPDVEAAGSTVKLSFS  DDTITDTAGFVAV
ID NO 10:   YYEADYTAQV GDKLSCSKGNCPEVEATGATVSYDFS  DSTITDTAGYIAV
ID NO 11:   YCSNNID SK DSNLTCTANACPSVEEASTTMLLEFDLTNDFGGTAGFLAA
ID NO 12:   YCSNNID SD DSNVTCTADACPSVEEASTKMLLEFDLTNNFGGTAGFLAA
ID NO 13:   YCDENLN ST GTKLTCSVGNCPLVEAASTQSLDEFNESSSYGNPAGYLAA
ID NO 14:   YCGKNNDAPA GTNITCTGNACPEVEKADATFLYSFE DSGVGDVTGFLAL
ID NO 15:   YQTTDAWPAS         RTVPKDTTLISSFD  HTLKGSSGYIAF

ID NO 1:    GEKEKTIYVV FRGTSSIRNA IADIVFVPVN YPPV   NGA KVHKGFLDSY
ID NO 2:    GENEKTIYVV FRGTSSIRNA IADIVFVPVN YPPV   NGA KVHKGFLDSY
ID NO 3:    GDSEKTIYIV FRGSSSIRNW IADLTFVPVS YPPV   SGT KVHKGFLDSY
ID NO 4:    SDKQKTIYLV FRGTNSFRSA ITDIVFNFSD YKPV   KGA KVHAGFLSSY
ID NO 5:    DDSSKEIITV FRGTGSDTNL QLDTNYTLTP FDTLPQCNCG EVHGGYYIGW
ID NO 6:    DDSSKEIITV FRGTGSDTNL QLDTNYTLTP FDTLPQCNSC EVHGGYYIGW
ID NO 7:    DSARKEIVVS FRGSINIRNW LTNLDFG QE DCSL   VSGC GVHSGFQRAW
ID NO 8:    DNARKEIVVS VRGSINVRNW ITNFNFG QK TCDL   VAGC GVHTGFLDAW
ID NO 9:    DNTNKAIVVA FRGSYSIRNW VTDATFP QT DPGL   CDGC KAELGFWTAW
ID NO 10:   DHTNSAVVLA FRGSYSVRNW VADATFV HT NPGL   CDGC LAELGFWSSW
ID NO 11:   DNTNKRLVVA FRGSSTIENW IANLDFILED NDDL   CTGC KVHTGFWKAW
ID NO 12:   DNTNKRLVVA FRGSSTIKNW IADLDFILQD NDDL   CTGC KVHTGFWKAW
ID NO 13:   DETNKLLVLS FRGSADLANW VANLNFGLED ASDL   CSGC EVHSGFWKAW
ID NO 14:   DNTNKLIVLS FRGSRSIENW IGNLNFDLKE INDI   CSGC RGHDGFTSSW
ID NO 15:   NEPCKEIIVA YRGTDSLIDW LTNLNFDKTA WPAN   ISNS LVHEGFLNAY
```

Figure 1

```
ID NO 1:    NEVQDKLVAE VKAQLDRHPG YKIVVTGHSL GGATAVLSALDLYHHGHA
ID NO 2:    NEVQDKLVAE VKAQLDRHPG YKIVVTGHSL GGATAVLSALDLYHHGHD
ID NO 3:    GEVQNELVAT VLDQFKQYPS YKVAVTGHSL GGATALLCALDLYQREEGLS
ID NO 4:    EQVVNDYFPV VQEQLTAHPT YKVIVTGHSL GGAQALLACMDLYQREPRLS
ID NO 5:    VSVQDQVESL VKQQVSQYPD YALTVTGHSL GASLAALTAAQL SATYD
ID NO 6:    ISVQDQVESL VQQQVSQFPD YALTVTGHSL GASLAALTAAQL SATYD
ID NO 7:    NEISSQATAA VASARKANPS FNVISTGHSL GGAVAVLAAANLRVGGT
ID NO 8:    EEVAANVKAA VSAAKTANPT FKFVVTGHSL GGAVATIAAAYLRKDGF
ID NO 9:    KVVRDRLIKT LDELKPEHSD YKIVVVGHSL GAATASLAAADLRTKNY
ID NO 10:   KLVRDDIIKE LKEVVAQNPN YELVVVGHSL GAAVATLAATDLRGKGYP
ID NO 11:   ESAADELTSK IKSAMSTYSG YTLYFTGHSL GGALATLGATVLRNDGY
ID NO 12:   EAAADNLTSK IKSAMSTYSG YTLYFTGHSL GGALATLGATVLRNDGY
ID NO 13:   SEIADTITSK VESALSDHSD YSLVLTGHSY GAALAALAATALRNSGH
ID NO 14:   RSVADTLRQK VEDAVREIPD YRVVFTGHSL GGALATVAGADLRGNGY
ID NO 15:   LVSMQQVQEA VDSLLAKCPD ATISFTGHSL GGALACISMVDTAQRHRGI

ID NO 1:     NIEIYTQG QPRIGTPAFA NYVIGT      KIPYQRLVHERDIVPEL
ID NO 2:     NIEIYTQG QPRIGTPEFA NYVIGT      KIPYQRLVNERDIVPEL
ID NO 3:    SSNLFLYTQG QPRVGDPAFA NYVVST     GIPYRRTVNERDIVPEL
ID NO 4:    PKNLSIFTVG GPRVGNPTFA YYVEST     GIPFQRTVHKRDIVPEV
ID NO 5:     NIRLYTFG EPRSCNQAFA SYMNDAFQASSPDTTQYFRVTHANDGIPNL
ID NO 6:     NIRLYTFG EPRS KQAFA SYMNDAFQASSPDTTQYFRVTHANDGIPNL
ID NO 7:     PVDIYTYG SPRVGNAQLS AFVSNQ       AGGEYRVTHADDPVPRL
ID NO 8:     PFDLYTYG SPRVGNDFFA NFVTQQ       TGAEYRVTHGDDPVPRL
ID NO 9:     DAILYAYA APRVANKPLA EFITNQ       GNNYRFTHNDDPVPKL
ID NO 10:    SAKLYAYA SPRVGNAALA KYITAQ       GNNRFTHTNDPVPKL
ID NO 11:    SVELYTYG CPRIGNYALA EHITSQ       GSGANFRVTHLNDIVPRV
ID NO 12:    SVELYTYG CPRVGNYALA EHITSQ       GSGANFPVTHLNDIVPRV
ID NO 13:    SVELYNYG QPRLGNEALA TYITDQ       NKGGNYRVTHTNDIVPKL
ID NO 14:    DIDVFSYG APRVCNRAFA EFLTVQ       TGGTLYRITHTNDIVPRL
ID NO 15:    KMQMFTYG QPRTGNQAFA EYVENL       GHPVFRVVYRHDIVPRM

ID NO 1:    PPGAFGFLHA GEEFWIMK          DSSLRVCPNGIETDNCSNSIV
ID NO 2:    PPGAFGFLHA GEEFWIMK          DSSLRVCPNGIETDNCSNSIV
ID NO 3:    PPAAFGFLHA GEEYWITD          NSPEFVQVCTSDLETSDCSNSIV
ID NO 4:    PPQSFGFLEP GVESWIKS          GTSNVQICTSEIETKDCSNSIV
ID NO 5:    PPVEQGYAEG GVEYWSV           DPYSAQNTFVCTGDEVQCCE AQGGQG
ID NO 6:    PPADEGYAEG VVEYWSV           DPYSAQNTFVCTGDEVQCCE AQGGQG
ID NO 7:    PPLIFGYRET TPEFWLSGGGGDKVDYTISDVKVCEGAANLG CNGGTL
ID NO 8:    PPIVFGYRET SPEYWLNG GPLDKDYTVTEIKVCEGIANVM CNGGTI
ID NO 9:    PLLTMGYVEI SPEYYITA PDNTTVTDNQVTVLDGYVNFK GNTGTS
ID NO 10:   PLLSMGYVEV SPEYWITS PNNATVSTSDIKVIDGDVSFD GNTGTG
ID NO 11:   PPMDFGFSQP SPEYWITS GNGASVTASDIEVIEGINSTA GNAGEA
ID NO 12:   PPMDFGFSQP SPEYWITS GTGASVTASDIELIEGINSTA GNAGEA
ID NO 13:   PPTLLGYHFF SPEYYISS ADEATVTTTDVTEVTGIDATG GNDGTD
ID NO 14:   PPREFGYSHS SPEYWIKS GTLVPVTRNDIVKIEGIDATG GNNQPN
ID NO 15:   PPMDLGFQHH GQEVWYEG          DENIKFCKGEGENLTCELGVP

ID NO 1:    PFT    SVIDHLSYLDMNTGL CL
ID NO 2:    PFT    SVIDHLSYLDMNTGL CL
ID NO 3:    PFT    SVIDHLSYFGINTGL CT
ID NO 4:    PFT    SILDHLSYFDIKEGS CL
ID NO 5:    VN     NAHTTYF GMTSGACTW
ID NO 6:    VN     NAHTTYF GMTSGHCTW

ID NO 7:    GL     DIAAHLHYF QATDA CNAGGFSWR R
ID NO 8:    GL     DILAHITYF QSMAT CAPIAIPWK R
ID NO 9:    GGLPDLLAFHSHVWYFIHADACKGPGLPLR
ID NO 10:   LPLLTDFEAHIWYF VQVDA GKGPGLPFK R
ID NO 11:   TV     SVLAHLWYF FAISE CLL
ID NO 12:   TV     DVLAHLWYF FAISE CLL
ID NO 13:   GT     SIDAHRWYF IYISE CS
ID NO 14:   IP     DIPAHLWYF GLIGT CL
ID NO 15:   FSEL NAKDHSEYP CMH
```

Figure 1 (cont.)

| ID NO: | Micro organism | SEQ ID NO.: |
|---|---|---|
| 1. | *Absidia reflexa* | 3 |
| 2. | *Absidia corymbifera* | 4 |
| 3. | *Rhizmucor miehei* | 5 |
| 4. | *Rhizopus delemar (oryzea)* | 6 |
| 5. | *Aspergillus niger* | 7 |
| 6. | *Aspergillus tubingensis* | 8 |
| 7. | *Fusarium oxysporum* | 9 |
| 8. | *Fusarium heterosporum* | 10 |
| 9. | *Aspergillus oryzae* | 11 |
| 10. | *Penicilium camembertii* | 12 |
| 11. | *Aspergillus foetidus* | 13 |
| 12 | *Aspergillus niger* | 14 |
| 13. | *Aspergillus oryzea* | 15 |
| 14. | *Thermomyces lanuginosus* | 2 |
| 15. | *Landerina penisapora* | 16 |

Figure 1. Alignment of lipase sequences.

US 9,163,203 B2

SEQUENCE LISTING

```
<160> NUMBER OF SEQ ID NOS: 16

<210> SEQ ID NO 1
<211> LENGTH: 873
<212> TYPE: DNA
<213> ORGANISM: Thermomyces lanuginosus
<220> FEATURE:
<221> NAME/KEY: CDS
<222> LOCATION: (1)..(873)
<220> FEATURE:
<221> NAME/KEY: sig_peptide
<222> LOCATION: (1)..(51)
<220> FEATURE:
<221> NAME/KEY: propep
<222> LOCATION: (52)..(66)
<220> FEATURE:
<221> NAME/KEY: mat_peptide
<222> LOCATION: (67)..()

<400> SEQUENCE: 1 atg agg agc tcc ctt gtg ctg ttc ttt gtc tct gcg tgg acg gcc ttg      48
Met Arg Ser Ser Leu Val Leu Phe Phe Val Ser Ala Trp Thr Ala Leu
        -20                 -15                 -10 gcc agt cct att cgt cga gag gtc tcg cag gat ctg ttt aac cag ttc      96
Ala Ser Pro Ile Arg Arg Glu Val Ser Gln Asp Leu Phe Asn Gln Phe
 -5                  -1  1               5                  10 aat ctc ttt gca cag tat tct gca gcc gca tac tgc gga aaa aac aat     144
Asn Leu Phe Ala Gln Tyr Ser Ala Ala Ala Tyr Cys Gly Lys Asn Asn
                 15                  20                  25 gat gcc cca gct ggt aca aac att acg tgc acg gga aat gcc tgc ccc     192
Asp Ala Pro Ala Gly Thr Asn Ile Thr Cys Thr Gly Asn Ala Cys Pro
```

|  |  |  |  | 30 |  |  |  | 35 |  |  |  | 40 |  |  |  |  |
|---|---|---|---|---|---|---|---|---|---|---|---|---|---|---|---|---|
| gag | gta | gag | aag | gcg | gat | gca | acg | ttt | ctc | tac | tcg | ttt | gaa | gac | tct | 240 |
| Glu | Val | Glu | Lys | Ala | Asp | Ala | Thr | Phe | Leu | Tyr | Ser | Phe | Glu | Asp | Ser |  |
|  |  | 45 |  |  |  | 50 |  |  |  | 55 |  |  |  |  |  |  |
| gga | gtg | ggc | gat | gtc | acc | ggc | ttc | ctt | gct | ctc | gac | aac | acg | aac | aaa | 288 |
| Gly | Val | Gly | Asp | Val | Thr | Gly | Phe | Leu | Ala | Leu | Asp | Asn | Thr | Asn | Lys |  |
| 60 |  |  |  |  | 65 |  |  |  |  | 70 |  |  |  |  |  |  |
| ttg | atc | gtc | ctc | tct | ttc | cgt | ggc | tct | cgt | tcc | ata | gag | aac | tgg | atc | 336 |
| Leu | Ile | Val | Leu | Ser | Phe | Arg | Gly | Ser | Arg | Ser | Ile | Glu | Asn | Trp | Ile |  |
| 75 |  |  |  |  | 80 |  |  |  |  | 85 |  |  |  |  | 90 |  |
| ggg | aat | ctt | aac | ttc | gac | ttg | aaa | gaa | ata | aat | gac | att | tgc | tcc | ggc | 384 |
| Gly | Asn | Leu | Asn | Phe | Asp | Leu | Lys | Glu | Ile | Asn | Asp | Ile | Cys | Ser | Gly |  |
|  |  |  |  | 95 |  |  |  |  | 100 |  |  |  |  | 105 |  |  |
| tgc | agg | gga | cat | gac | ggc | ttc | act | tcg | tcc | tgg | agg | tct | gta | gcc | gat | 432 |
| Cys | Arg | Gly | His | Asp | Gly | Phe | Thr | Ser | Ser | Trp | Arg | Ser | Val | Ala | Asp |  |
|  |  |  | 110 |  |  |  |  | 115 |  |  |  |  | 120 |  |  |  |
| acg | tta | agg | cag | aag | gtg | gag | gat | gct | gtg | agg | gag | cat | ccc | gac | tat | 480 |
| Thr | Leu | Arg | Gln | Lys | Val | Glu | Asp | Ala | Val | Arg | Glu | His | Pro | Asp | Tyr |  |
|  |  |  | 125 |  |  |  |  | 130 |  |  |  |  | 135 |  |  |  |
| cgc | gtg | gtg | ttt | acc | gga | cat | agc | ttg | ggt | ggt | gca | ttg | gca | act | gtt | 528 |
| Arg | Val | Val | Phe | Thr | Gly | His | Ser | Leu | Gly | Gly | Ala | Leu | Ala | Thr | Val |  |
|  | 140 |  |  |  |  | 145 |  |  |  |  | 150 |  |  |  |  |  |
| gcc | gga | gca | gac | ctg | cgt | gga | aat | ggg | tat | gat | atc | gac | gtg | ttt | tca | 576 |
| Ala | Gly | Ala | Asp | Leu | Arg | Gly | Asn | Gly | Tyr | Asp | Ile | Asp | Val | Phe | Ser |  |
| 155 |  |  |  |  | 160 |  |  |  |  | 165 |  |  |  |  | 170 |  |
| tat | ggc | gcc | ccc | cga | gtc | gga | aac | agg | gct | ttt | gca | gaa | ttc | ctg | acc | 624 |
| Tyr | Gly | Ala | Pro | Arg | Val | Gly | Asn | Arg | Ala | Phe | Ala | Glu | Phe | Leu | Thr |  |
|  |  |  | 175 |  |  |  |  | 180 |  |  |  |  | 185 |  |  |  |
| gta | cag | acc | ggc | gga | aca | ctc | tac | cgc | att | acc | cac | acc | aat | gat | att | 672 |
| Val | Gln | Thr | Gly | Gly | Thr | Leu | Tyr | Arg | Ile | Thr | His | Thr | Asn | Asp | Ile |  |
|  |  |  | 190 |  |  |  |  | 195 |  |  |  |  | 200 |  |  |  |
| gtc | cct | aga | ctc | ccg | ccg | cgc | gaa | ttc | ggt | tac | agc | cat | tct | agc | cca | 720 |
| Val | Pro | Arg | Leu | Pro | Pro | Arg | Glu | Phe | Gly | Tyr | Ser | His | Ser | Ser | Pro |  |
|  |  | 205 |  |  |  |  | 210 |  |  |  |  | 215 |  |  |  |  |
| gag | tac | tgg | atc | aaa | tct | gga | acc | ctt | gtc | ccc | gtc | acc | cga | aac | gat | 768 |
| Glu | Tyr | Trp | Ile | Lys | Ser | Gly | Thr | Leu | Val | Pro | Val | Thr | Arg | Asn | Asp |  |
|  | 220 |  |  |  |  | 225 |  |  |  |  | 230 |  |  |  |  |  |
| atc | gtg | aag | ata | gaa | ggc | atc | gat | gcc | acc | ggc | ggc | aat | aac | cag | cct | 816 |
| Ile | Val | Lys | Ile | Glu | Gly | Ile | Asp | Ala | Thr | Gly | Gly | Asn | Asn | Gln | Pro |  |
| 235 |  |  |  |  | 240 |  |  |  |  | 245 |  |  |  |  | 250 |  |
| aac | att | ccg | gat | atc | cct | gcg | cac | cta | tgg | tac | ttc | ggg | tta | att | ggg | 864 |
| Asn | Ile | Pro | Asp | Ile | Pro | Ala | His | Leu | Trp | Tyr | Phe | Gly | Leu | Ile | Gly |  |
|  |  |  | 255 |  |  |  |  | 260 |  |  |  |  | 265 |  |  |  |
| aca | tgt | ctt |  |  |  |  |  |  |  |  |  |  |  |  |  | 873 |
| Thr | Cys | Leu |  |  |  |  |  |  |  |  |  |  |  |  |  |  |

<210> SEQ ID NO 2
<211> LENGTH: 291
<212> TYPE: PRT
<213> ORGANISM: Thermomyces lanuginosus

<400> SEQUENCE: 2

Met Arg Ser Ser Leu Val Leu Phe Phe Val Ser Ala Trp Thr Ala Leu
        -20              -15              -10

Ala Ser Pro Ile Arg Arg Glu Val Ser Gln Asp Leu Phe Asn Gln Phe
    -5              -1  1              5                   10

Asn Leu Phe Ala Gln Tyr Ser Ala Ala Tyr Cys Gly Lys Asn Asn
                15                  20                  25

Asp Ala Pro Ala Gly Thr Asn Ile Thr Cys Thr Gly Asn Ala Cys Pro

```
            30                  35                  40
Glu Val Glu Lys Ala Asp Ala Thr Phe Leu Tyr Ser Phe Glu Asp Ser
         45                  50                  55

Gly Val Gly Asp Val Thr Gly Phe Leu Ala Leu Asp Asn Thr Asn Lys
 60                  65                  70

Leu Ile Val Leu Ser Phe Arg Gly Ser Arg Ser Ile Glu Asn Trp Ile
 75                  80                  85                  90

Gly Asn Leu Asn Phe Asp Leu Lys Glu Ile Asn Asp Ile Cys Ser Gly
                 95                 100                 105

Cys Arg Gly His Asp Gly Phe Thr Ser Ser Trp Arg Ser Val Ala Asp
                110                 115                 120

Thr Leu Arg Gln Lys Val Glu Asp Ala Val Arg Glu His Pro Asp Tyr
                125                 130                 135

Arg Val Val Phe Thr Gly His Ser Leu Gly Gly Ala Leu Ala Thr Val
                140                 145                 150

Ala Gly Ala Asp Leu Arg Gly Asn Gly Tyr Asp Ile Asp Val Phe Ser
155                 160                 165                 170

Tyr Gly Ala Pro Arg Val Gly Asn Arg Ala Phe Ala Glu Phe Leu Thr
                175                 180                 185

Val Gln Thr Gly Gly Thr Leu Tyr Arg Ile Thr His Thr Asn Asp Ile
                190                 195                 200

Val Pro Arg Leu Pro Pro Arg Glu Phe Gly Tyr Ser His Ser Ser Pro
                205                 210                 215

Glu Tyr Trp Ile Lys Ser Gly Thr Leu Val Pro Val Thr Arg Asn Asp
                220                 225                 230

Ile Val Lys Ile Glu Gly Ile Asp Ala Thr Gly Gly Asn Asn Gln Pro
235                 240                 245                 250

Asn Ile Pro Asp Ile Pro Ala His Leu Trp Tyr Phe Gly Leu Ile Gly
                255                 260                 265

Thr Cys Leu

<210> SEQ ID NO 3
<211> LENGTH: 265
<212> TYPE: PRT
<213> ORGANISM: Absidia reflexa

<400> SEQUENCE: 3

Ser Ser Ser Ser Thr Gln Asp Tyr Arg Ile Ala Ser Glu Ala Glu Ile
 1               5                  10                  15

Lys Ala His Thr Phe Tyr Thr Ala Leu Ser Ala Asn Ala Tyr Cys Arg
                 20                  25                  30

Thr Val Ile Pro Gly Gly Arg Trp Ser Cys Pro His Cys Gly Val Ala
                 35                  40                  45

Ser Asn Leu Gln Ile Thr Lys Thr Phe Ser Thr Leu Ile Thr Asp Thr
             50                  55                  60

Asn Val Leu Val Ala Val Gly Glu Lys Glu Lys Thr Ile Tyr Val Val
 65                  70                  75                  80

Phe Arg Gly Thr Ser Ser Ile Arg Asn Ala Ile Ala Asp Ile Val Phe
                 85                  90                  95

Val Pro Val Asn Tyr Pro Pro Val Asn Gly Ala Lys Val His Lys Gly
                100                 105                 110

Phe Leu Asp Ser Tyr Asn Glu Val Gln Asp Lys Leu Val Ala Glu Val
                115                 120                 125

Lys Ala Gln Leu Asp Arg His Pro Gly Tyr Lys Ile Val Val Thr Gly
```

```
                 130                 135                 140
His Ser Leu Gly Gly Ala Thr Ala Val Leu Ser Ala Leu Asp Leu Tyr
145                 150                 155                 160

His His Gly His Ala Asn Ile Glu Ile Tyr Thr Gln Gly Gln Pro Arg
                165                 170                 175

Ile Gly Thr Pro Ala Phe Ala Asn Tyr Val Ile Gly Thr Lys Ile Pro
            180                 185                 190

Tyr Gln Arg Leu Val His Glu Arg Asp Ile Val Pro His Leu Pro Pro
        195                 200                 205

Gly Ala Phe Gly Phe Leu His Ala Gly Glu Glu Phe Trp Ile Met Lys
    210                 215                 220

Asp Ser Ser Leu Arg Val Cys Pro Asn Gly Ile Glu Thr Asp Asn Cys
225                 230                 235                 240

Ser Asn Ser Ile Val Pro Phe Thr Ser Val Ile Asp His Leu Ser Tyr
                245                 250                 255

Leu Asp Met Asn Thr Gly Leu Cys Leu
                260                 265

<210> SEQ ID NO 4
<211> LENGTH: 264
<212> TYPE: PRT
<213> ORGANISM: Absidia corymbifera

<400> SEQUENCE: 4

Ser Ser Ser Thr Gln Asp Tyr Arg Ile Ala Ser Glu Ala Glu Ile Lys
1               5                   10                  15

Ala His Thr Phe Tyr Thr Ala Leu Ser Ala Asn Ala Tyr Cys Arg Thr
            20                  25                  30

Val Ile Pro Gly Gly Gln Trp Ser Cys Pro His Cys Asp Val Ala Pro
        35                  40                  45

Asn Leu Asn Ile Thr Lys Thr Phe Thr Thr Leu Ile Thr Asp Thr Asn
    50                  55                  60

Val Leu Val Ala Val Gly Glu Asn Glu Lys Thr Ile Tyr Val Val Phe
65                  70                  75                  80

Arg Gly Thr Ser Ser Ile Arg Asn Ala Ile Ala Asp Ile Val Phe Val
                85                  90                  95

Pro Val Asn Tyr Pro Pro Val Asn Gly Ala Lys Val His Lys Gly Phe
            100                 105                 110

Leu Asp Ser Tyr Asn Glu Val Gln Asp Lys Leu Val Ala Glu Val Lys
        115                 120                 125

Ala Gln Leu Asp Arg His Pro Gly Tyr Lys Ile Val Val Thr Gly His
    130                 135                 140

Ser Leu Gly Gly Ala Thr Ala Val Leu Ser Ala Leu Asp Leu Tyr His
145                 150                 155                 160

His Gly His Asp Asn Ile Glu Ile Tyr Thr Gln Gly Gln Pro Arg Ile
                165                 170                 175

Gly Thr Pro Glu Phe Ala Asn Tyr Val Ile Gly Thr Lys Ile Pro Tyr
            180                 185                 190

Gln Arg Leu Val Asn Glu Arg Asp Ile Val Pro His Leu Pro Pro Gly
        195                 200                 205

Ala Phe Gly Phe Leu His Ala Gly Glu Glu Phe Trp Ile Met Lys Asp
    210                 215                 220

Ser Ser Leu Arg Val Cys Pro Asn Gly Ile Glu Thr Asp Asn Cys Ser
225                 230                 235                 240
```

```
Asn Ser Ile Val Pro Phe Thr Ser Val Ile Asp His Leu Ser Tyr Leu
                245                 250                 255

Asp Met Asn Thr Gly Leu Cys Leu
            260

<210> SEQ ID NO 5
<211> LENGTH: 269
<212> TYPE: PRT
<213> ORGANISM: Rhizomucor miehei

<400> SEQUENCE: 5

Ser Ile Asp Gly Gly Ile Arg Ala Ala Thr Ser Gln Glu Ile Asn Glu
1               5                   10                  15

Leu Thr Tyr Tyr Thr Thr Leu Ser Ala Asn Ser Tyr Cys Arg Thr Val
            20                  25                  30

Ile Pro Gly Ala Thr Trp Asp Cys Ile His Cys Asp Ala Thr Glu Asp
        35                  40                  45

Leu Lys Ile Ile Lys Thr Trp Ser Thr Leu Ile Tyr Asp Thr Asn Ala
    50                  55                  60

Met Val Ala Arg Gly Asp Ser Glu Lys Thr Ile Tyr Ile Val Phe Arg
65                  70                  75                  80

Gly Ser Ser Ser Ile Arg Asn Trp Ile Ala Asp Leu Thr Phe Val Pro
                85                  90                  95

Val Ser Tyr Pro Pro Val Ser Gly Thr Lys Val His Lys Gly Phe Leu
            100                 105                 110

Asp Ser Tyr Gly Glu Val Gln Asn Glu Leu Val Ala Thr Val Leu Asp
        115                 120                 125

Gln Phe Lys Gln Tyr Pro Ser Tyr Lys Val Ala Val Thr Gly His Ser
    130                 135                 140

Leu Gly Gly Ala Thr Ala Leu Leu Cys Ala Leu Asp Leu Tyr Gln Arg
145                 150                 155                 160

Glu Glu Gly Leu Ser Ser Ser Asn Leu Phe Leu Tyr Thr Gln Gly Gln
                165                 170                 175

Pro Arg Val Gly Asp Pro Ala Phe Ala Asn Tyr Val Val Ser Thr Gly
            180                 185                 190

Ile Pro Tyr Arg Arg Thr Val Asn Glu Arg Asp Ile Val Pro His Leu
        195                 200                 205

Pro Pro Ala Ala Phe Gly Phe Leu His Ala Gly Glu Glu Tyr Trp Ile
    210                 215                 220

Thr Asp Asn Ser Pro Glu Thr Val Gln Val Cys Thr Ser Asp Leu Glu
225                 230                 235                 240

Thr Ser Asp Cys Ser Asn Ser Ile Val Pro Phe Thr Ser Val Leu Asp
                245                 250                 255

His Leu Ser Tyr Phe Gly Ile Asn Thr Gly Leu Cys Thr
            260                 265

<210> SEQ ID NO 6
<211> LENGTH: 271
<212> TYPE: PRT
<213> ORGANISM: Rhizopus oryzae

<400> SEQUENCE: 6

Ser Ala Ser Asp Gly Gly Lys Val Val Ala Ala Thr Thr Ala Gln Ile
1               5                   10                  15

Gln Glu Phe Thr Lys Tyr Ala Gly Ile Ala Ala Thr Ala Tyr Cys Arg
            20                  25                  30
```

```
Ser Val Val Pro Gly Asn Lys Trp Asp Cys Val Gln Cys Gln Lys Trp
         35                  40                  45

Val Pro Asp Gly Lys Ile Ile Thr Thr Phe Thr Ser Leu Leu Ser Asp
 50                  55                  60

Thr Asn Gly Tyr Val Leu Arg Ser Asp Lys Gln Lys Thr Ile Tyr Leu
 65                  70                  75                  80

Val Phe Arg Gly Thr Asn Ser Phe Arg Ser Ala Ile Thr Asp Ile Val
                 85                  90                  95

Phe Asn Phe Ser Asp Tyr Lys Pro Val Lys Gly Ala Lys Val His Ala
            100                 105                 110

Gly Phe Leu Ser Ser Tyr Glu Gln Val Asn Asp Tyr Phe Pro Val
            115                 120                 125

Val Gln Glu Gln Leu Thr Ala His Pro Thr Tyr Lys Val Ile Val Thr
130                 135                 140

Gly His Ser Leu Gly Gly Ala Gln Ala Leu Leu Ala Gly Met Asp Leu
145                 150                 155                 160

Tyr Gln Arg Glu Pro Arg Leu Ser Pro Lys Asn Leu Ser Ile Phe Thr
                165                 170                 175

Val Gly Gly Pro Arg Val Gly Asn Pro Thr Phe Ala Tyr Tyr Val Glu
            180                 185                 190

Ser Thr Gly Ile Pro Phe Gln Arg Thr Val His Lys Arg Asp Ile Val
        195                 200                 205

Pro His Val Pro Pro Gln Ser Phe Gly Phe Leu His Pro Gly Val Glu
    210                 215                 220

Ser Trp Ile Lys Ser Gly Thr Ser Asn Val Gln Ile Cys Thr Ser Glu
225                 230                 235                 240

Ile Glu Thr Lys Asp Cys Ser Asn Ser Ile Val Pro Phe Thr Ser Ile
                245                 250                 255

Leu Asp His Leu Ser Tyr Phe Asp Ile Asn Glu Gly Ser Cys Leu
            260                 265                 270

<210> SEQ ID NO 7
<211> LENGTH: 267
<212> TYPE: PRT
<213> ORGANISM: Aspergillus niger

<400> SEQUENCE: 7

Thr Ala Gly His Ala Leu Ala Ala Ser Thr Gln Gly Ile Ser Glu Asp
 1               5                  10                  15

Leu Tyr Ser Arg Leu Val Glu Met Ala Thr Ile Ser Gln Ala Ala Tyr
                 20                  25                  30

Ala Asp Leu Cys Asn Ile Pro Ser Thr Ile Ile Lys Gly Glu Lys Ile
             35                  40                  45

Tyr Asn Ser Gln Thr Asp Ile Asn Gly Trp Ile Leu Arg Asp Asp Ser
         50                  55                  60

Ser Lys Glu Ile Ile Thr Val Phe Arg Gly Thr Gly Ser Asp Thr Asn
 65                  70                  75                  80

Leu Gln Leu Asp Thr Asn Tyr Thr Leu Thr Pro Phe Asp Thr Leu Pro
                 85                  90                  95

Gln Cys Asn Gly Cys Glu Val His Gly Gly Tyr Tyr Ile Gly Trp Val
            100                 105                 110

Ser Val Gln Asp Gln Val Glu Ser Leu Val Lys Gln Gln Val Ser Gln
            115                 120                 125

Tyr Pro Asp Tyr Ala Leu Thr Val Thr Gly His Ser Leu Gly Ala Ser
130                 135                 140
```

```
Leu Ala Leu Thr Ala Ala Gln Leu Ser Ala Thr Tyr Asp Asn Ile
145                 150                 155                 160

Arg Leu Tyr Thr Phe Gly Glu Pro Arg Ser Gly Asn Gln Ala Phe Ala
                165                 170                 175

Ser Tyr Met Asn Asp Ala Phe Gln Ala Ser Ser Pro Asp Thr Thr Gln
            180                 185                 190

Tyr Phe Arg Val Thr His Ala Asn Asp Gly Ile Pro Asn Leu Pro Pro
        195                 200                 205

Val Glu Gln Gly Tyr Ala His Gly Gly Val Glu Tyr Trp Ser Val Asp
    210                 215                 220

Pro Tyr Ser Ala Gln Asn Thr Phe Val Cys Thr Gly Asp Glu Val Gln
225                 230                 235                 240

Cys Cys Glu Ala Gln Gly Gly Gln Gly Val Asn Asn Ala His Thr Thr
                245                 250                 255

Tyr Phe Gly Met Thr Ser Gly Ala Cys Thr Trp
            260                 265

<210> SEQ ID NO 8
<211> LENGTH: 266
<212> TYPE: PRT
<213> ORGANISM: Aspergillus tubingensis

<400> SEQUENCE: 8

Thr Ala Gly His Ala Leu Ala Ala Ser Thr Gln Gly Ile Ser Glu Asp
1               5                   10                  15

Leu Tyr Ser Arg Leu Val Glu Met Ala Thr Ile Ser Gln Ala Ala Tyr
                20                  25                  30

Ala Asp Leu Cys Asn Ile Pro Ser Thr Ile Ile Lys Gly Glu Lys Ile
            35                  40                  45

Tyr Asn Ser Gln Thr Asp Ile Asn Gly Trp Ile Leu Arg Asp Asp Ser
        50                  55                  60

Ser Lys Glu Ile Ile Thr Val Phe Arg Gly Thr Gly Ser Asp Thr Asn
65                  70                  75                  80

Leu Gln Leu Asp Thr Asn Tyr Thr Leu Thr Pro Phe Asp Thr Leu Pro
                85                  90                  95

Gln Cys Asn Ser Cys Glu Val His Gly Gly Tyr Tyr Ile Gly Trp Ile
            100                 105                 110

Ser Val Gln Asp Gln Val Glu Ser Leu Val Gln Gln Gln Val Ser Gln
        115                 120                 125

Phe Pro Asp Tyr Ala Leu Thr Val Thr Gly His Ser Leu Gly Ala Ser
130                 135                 140

Leu Ala Ala Leu Thr Ala Ala Gln Leu Ser Ala Thr Tyr Asp Asn Ile
145                 150                 155                 160

Arg Leu Tyr Thr Phe Gly Glu Pro Arg Ser Asn Gln Ala Phe Ala Ser
                165                 170                 175

Tyr Met Asn Asp Ala Phe Gln Ala Ser Ser Pro Asp Thr Thr Gln Tyr
            180                 185                 190

Phe Arg Val Thr His Ala Asn Asp Gly Ile Pro Asn Leu Pro Pro Ala
        195                 200                 205

Asp Glu Gly Tyr Ala His Gly Val Val Glu Tyr Trp Ser Val Asp Pro
    210                 215                 220

Tyr Ser Ala Gln Asn Thr Phe Val Cys Thr Gly Asp Glu Val Gln Cys
225                 230                 235                 240

Cys Glu Ala Gln Gly Gly Gln Gly Val Asn Asn Ala His Thr Thr Tyr
```

```
                      245                 250                 255
Phe Gly Met Thr Ser Gly His Cys Thr Trp
            260                 265

<210> SEQ ID NO 9
<211> LENGTH: 276
<212> TYPE: PRT
<213> ORGANISM: Fusarium oxysporum

<400> SEQUENCE: 9

Ala Val Gly Val Thr Thr Asp Phe Ser Asn Phe Lys Phe Tyr Ile
1               5                   10                  15

Gln His Gly Ala Ala Tyr Cys Asn Ser Glu Ala Ala Gly Ser
            20                  25                  30

Lys Ile Thr Cys Ser Asn Asn Gly Cys Pro Thr Val Gln Gly Asn Gly
            35                  40                  45

Ala Thr Ile Val Thr Ser Phe Val Gly Ser Lys Thr Gly Ile Gly Gly
        50                  55                  60

Tyr Val Ala Thr Asp Ser Ala Arg Lys Glu Ile Val Val Ser Phe Arg
65                  70                  75                  80

Gly Ser Ile Asn Ile Arg Asn Trp Leu Thr Asn Leu Asp Phe Gly Gln
                85                  90                  95

Glu Asp Cys Ser Leu Val Ser Gly Cys Gly Val His Ser Gly Phe Gln
            100                 105                 110

Arg Ala Trp Asn Glu Ile Ser Ser Gln Ala Thr Ala Ala Val Ala Ser
        115                 120                 125

Ala Arg Lys Ala Asn Pro Ser Phe Asn Val Ile Ser Thr Gly His Ser
130                 135                 140

Leu Gly Gly Ala Val Ala Val Leu Ala Ala Asn Leu Arg Val Gly
145                 150                 155                 160

Gly Thr Pro Val Asp Ile Tyr Thr Tyr Gly Ser Pro Arg Val Gly Asn
                165                 170                 175

Ala Gln Leu Ser Ala Phe Val Ser Asn Gln Ala Gly Gly Glu Tyr Arg
            180                 185                 190

Val Thr His Ala Asp Asp Pro Val Pro Arg Leu Pro Pro Leu Ile Phe
        195                 200                 205

Gly Tyr Arg His Thr Thr Pro Glu Phe Trp Leu Ser Gly Gly Gly Gly
210                 215                 220

Asp Lys Val Asp Tyr Thr Ile Ser Asp Val Lys Val Cys Glu Gly Ala
225                 230                 235                 240

Ala Asn Leu Gly Cys Asn Gly Gly Thr Leu Gly Leu Asp Ile Ala Ala
                245                 250                 255

His Leu His Tyr Phe Gln Ala Thr Asp Ala Cys Asn Ala Gly Gly Phe
            260                 265                 270

Ser Trp Arg Arg
        275

<210> SEQ ID NO 10
<211> LENGTH: 273
<212> TYPE: PRT
<213> ORGANISM: Fusarium heterosporum

<400> SEQUENCE: 10

Thr Val Thr Thr Gln Asp Leu Ser Asn Phe Arg Phe Tyr Leu Gln His
1               5                   10                  15

Ala Asp Ala Ala Tyr Cys Asn Phe Asn Thr Ala Val Gly Lys Pro Val
```

```
                20                  25                  30
His Cys Ser Ala Gly Asn Cys Pro Asp Ile Glu Lys Asp Ala Ala Ile
            35                  40                  45

Val Val Gly Ser Val Gly Thr Lys Thr Gly Ile Gly Ala Tyr Val
 50                  55                  60

Ala Thr Asp Asn Ala Arg Lys Glu Ile Val Ser Val Arg Gly Ser
 65                  70                  75                  80

Ile Asn Val Arg Asn Trp Ile Thr Asn Phe Asn Phe Gly Gln Lys Thr
                85                  90                  95

Cys Asp Leu Val Ala Gly Cys Gly Val His Thr Gly Phe Leu Asp Ala
            100                 105                 110

Trp Glu Glu Val Ala Ala Asn Val Lys Ala Ala Val Ser Ala Ala Lys
            115                 120                 125

Thr Ala Asn Pro Thr Phe Lys Phe Val Val Thr Gly His Ser Leu Gly
            130                 135                 140

Gly Ala Val Ala Thr Ile Ala Ala Ala Tyr Leu Arg Lys Asp Gly Phe
145                 150                 155                 160

Pro Phe Asp Leu Tyr Thr Tyr Gly Ser Pro Arg Val Gly Asn Asp Phe
                165                 170                 175

Phe Ala Asn Phe Val Thr Gln Gln Thr Gly Ala Glu Tyr Arg Val Thr
                180                 185                 190

His Gly Asp Asp Pro Val Pro Arg Leu Pro Pro Ile Val Phe Gly Tyr
            195                 200                 205

Arg His Thr Ser Pro Glu Tyr Trp Leu Asn Gly Gly Pro Leu Asp Lys
            210                 215                 220

Asp Tyr Thr Val Thr Glu Ile Lys Val Cys Glu Gly Ile Ala Asn Val
225                 230                 235                 240

Met Cys Asn Gly Gly Thr Ile Gly Leu Asp Ile Leu Ala His Ile Thr
                245                 250                 255

Tyr Phe Gln Ser Met Ala Thr Cys Ala Pro Ile Ala Ile Pro Trp Lys
                260                 265                 270

Arg

<210> SEQ ID NO 11
<211> LENGTH: 278
<212> TYPE: PRT
<213> ORGANISM: Aspergillus oryzae

<400> SEQUENCE: 11

Asp Ile Pro Thr Thr Gln Leu Glu Asp Phe Lys Phe Trp Val Gln Tyr
 1               5                  10                  15

Ala Ala Ala Thr Tyr Cys Pro Asn Asn Tyr Val Ala Lys Asp Gly Glu
                20                  25                  30

Lys Leu Asn Cys Ser Val Gly Asn Cys Pro Asp Val Glu Ala Ala Gly
            35                  40                  45

Ser Thr Val Lys Leu Ser Phe Ser Asp Thr Ile Thr Asp Thr Ala
        50                  55                  60

Gly Phe Val Ala Val Asp Asn Thr Asn Lys Ala Ile Val Val Ala Phe
 65                  70                  75                  80

Arg Gly Ser Tyr Ser Ile Arg Asn Trp Val Thr Asp Ala Thr Phe Pro
                85                  90                  95

Gln Thr Asp Pro Gly Leu Cys Asp Gly Cys Lys Ala Glu Leu Gly Phe
            100                 105                 110

Trp Thr Ala Trp Lys Val Val Arg Asp Arg Ile Ile Lys Thr Leu Asp
```

```
            115                 120                 125
Glu Leu Lys Pro Glu His Ser Asp Tyr Lys Ile Val Val Gly His
    130                 135                 140

Ser Leu Gly Ala Ala Ile Ala Ser Leu Ala Ala Ala Asp Leu Arg Thr
145                 150                 155                 160

Lys Asn Tyr Asp Ala Ile Leu Tyr Ala Ala Ala Pro Arg Val Ala
                165                 170                 175

Asn Lys Pro Leu Ala Glu Phe Ile Thr Asn Gln Gly Asn Asn Tyr Arg
            180                 185                 190

Phe Thr His Asn Asp Asp Pro Val Pro Lys Leu Pro Leu Leu Thr Met
                195                 200                 205

Gly Tyr Val His Ile Ser Pro Glu Tyr Tyr Ile Thr Ala Pro Asp Asn
    210                 215                 220

Thr Thr Val Thr Asp Asn Gln Val Thr Val Leu Asp Gly Tyr Val Asn
225                 230                 235                 240

Phe Lys Gly Asn Thr Gly Thr Ser Gly Gly Leu Pro Asp Leu Leu Ala
                245                 250                 255

Phe His Ser His Val Trp Tyr Phe Ile His Ala Asp Ala Cys Lys Gly
            260                 265                 270

Pro Gly Leu Pro Leu Arg
            275

<210> SEQ ID NO 12
<211> LENGTH: 278
<212> TYPE: PRT
<213> ORGANISM: Penicillium camemberti

<400> SEQUENCE: 12

Asp Val Ser Thr Ser Glu Leu Asp Gln Phe Glu Phe Trp Val Gln Tyr
1               5                   10                  15

Ala Ala Ala Ser Tyr Tyr Glu Ala Asp Tyr Thr Ala Gln Val Gly Asp
                20                  25                  30

Lys Leu Ser Cys Ser Lys Gly Asn Cys Pro Glu Val Glu Ala Thr Gly
            35                  40                  45

Ala Thr Val Ser Tyr Asp Phe Ser Asp Ser Thr Ile Thr Asp Thr Ala
        50                  55                  60

Gly Tyr Ile Ala Val Asp His Thr Asn Ser Ala Val Val Leu Ala Phe
65                  70                  75                  80

Arg Gly Ser Tyr Ser Val Arg Asn Trp Val Ala Asp Ala Thr Phe Val
                85                  90                  95

His Thr Asn Pro Gly Leu Cys Asp Gly Cys Leu Ala Glu Leu Gly Phe
            100                 105                 110

Trp Ser Ser Trp Lys Leu Val Arg Asp Asp Ile Ile Lys Glu Leu Lys
        115                 120                 125

Glu Val Val Ala Gln Asn Pro Asn Tyr Glu Leu Val Val Val Gly His
    130                 135                 140

Ser Leu Gly Ala Ala Val Ala Thr Leu Ala Ala Thr Asp Leu Arg Gly
145                 150                 155                 160

Lys Gly Tyr Pro Ser Ala Lys Leu Tyr Ala Tyr Ala Ser Pro Arg Val
                165                 170                 175

Gly Asn Ala Ala Leu Ala Lys Tyr Ile Thr Ala Gln Gly Asn Asn Phe
            180                 185                 190

Arg Phe Thr His Thr Asn Asp Pro Val Pro Lys Leu Pro Leu Leu Ser
        195                 200                 205
```

```
Met Gly Tyr Val His Val Ser Pro Glu Tyr Trp Ile Thr Pro Asn
    210                 215                 220

Asn Ala Thr Val Ser Thr Ser Asp Ile Lys Val Ile Asp Gly Asp Val
225                 230                 235                 240

Ser Phe Asp Gly Asn Thr Gly Thr Gly Leu Pro Leu Leu Thr Asp Phe
                245                 250                 255

Glu Ala His Ile Trp Tyr Phe Val Gln Val Asp Ala Gly Lys Gly Pro
                260                 265                 270

Gly Leu Pro Phe Lys Arg
                275

<210> SEQ ID NO 13
<211> LENGTH: 270
<212> TYPE: PRT
<213> ORGANISM: Aspergillus foetidus

<400> SEQUENCE: 13

Ser Val Ser Thr Ser Thr Leu Asp Glu Leu Gln Leu Phe Ala Gln Trp
1               5                   10                  15

Ser Ala Ala Tyr Cys Ser Asn Asn Ile Asp Ser Lys Asp Ser Asn
                20                  25                  30

Leu Thr Cys Thr Ala Asn Ala Cys Pro Ser Val Glu Glu Ala Ser Thr
            35                  40                  45

Thr Met Leu Leu Glu Phe Asp Leu Thr Asn Asp Phe Gly Gly Thr Ala
    50                  55                  60

Gly Phe Leu Ala Ala Asp Asn Thr Asn Lys Arg Leu Val Val Ala Phe
65                  70                  75                  80

Arg Gly Ser Ser Thr Ile Glu Asn Trp Ile Ala Asn Leu Asp Phe Ile
                85                  90                  95

Leu Glu Asp Asn Asp Asp Leu Cys Thr Gly Cys Lys Val His Thr Gly
                100                 105                 110

Phe Trp Lys Ala Trp Glu Ser Ala Ala Asp Glu Leu Thr Ser Lys Ile
            115                 120                 125

Lys Ser Ala Met Ser Thr Tyr Ser Gly Tyr Thr Leu Tyr Phe Thr Gly
    130                 135                 140

His Ser Leu Gly Gly Ala Leu Ala Thr Leu Gly Ala Thr Val Leu Arg
145                 150                 155                 160

Asn Asp Gly Tyr Ser Val Glu Leu Tyr Thr Tyr Gly Cys Pro Arg Ile
                165                 170                 175

Gly Asn Tyr Ala Leu Ala Glu His Ile Thr Ser Gln Gly Ser Gly Ala
            180                 185                 190

Asn Phe Arg Val Thr His Leu Asn Asp Ile Val Pro Arg Val Pro Pro
    195                 200                 205

Met Asp Phe Gly Phe Ser Gln Pro Ser Pro Glu Tyr Trp Ile Thr Ser
    210                 215                 220

Gly Asn Gly Ala Ser Val Thr Ala Ser Asp Ile Glu Val Ile Glu Gly
225                 230                 235                 240

Ile Asn Ser Thr Ala Gly Asn Ala Gly Glu Ala Thr Val Ser Val Leu
                245                 250                 255

Ala His Leu Trp Tyr Phe Phe Ala Ile Ser Glu Cys Leu Leu
            260                 265                 270

<210> SEQ ID NO 14
<211> LENGTH: 270
<212> TYPE: PRT
<213> ORGANISM: Aspergillus niger
```

<400> SEQUENCE: 14

```
Ser Val Ser Thr Ser Thr Leu Asp Glu Leu Gln Leu Phe Ser Gln Trp
 1               5                  10                  15
Ser Ala Ala Ala Tyr Cys Ser Asn Asn Ile Asp Ser Asp Asp Ser Asn
             20                  25                  30
Val Thr Cys Thr Ala Asp Ala Cys Pro Ser Val Glu Glu Ala Ser Thr
         35                  40                  45
Lys Met Leu Leu Glu Phe Asp Leu Thr Asn Asn Phe Gly Gly Thr Ala
 50                  55                  60
Gly Phe Leu Ala Ala Asp Asn Thr Asn Lys Arg Leu Val Val Ala Phe
 65                  70                  75                  80
Arg Gly Ser Ser Thr Ile Lys Asn Trp Ile Ala Asp Leu Asp Phe Ile
                 85                  90                  95
Leu Gln Asp Asn Asp Asp Leu Cys Thr Gly Cys Lys Val His Thr Gly
                100                 105                 110
Phe Trp Lys Ala Trp Glu Ala Ala Asp Asn Leu Thr Ser Lys Ile
             115                 120                 125
Lys Ser Ala Met Ser Thr Tyr Ser Gly Tyr Thr Leu Tyr Phe Thr Gly
130                 135                 140
His Ser Leu Gly Gly Ala Leu Ala Thr Leu Gly Ala Thr Val Leu Arg
145                 150                 155                 160
Asn Asp Gly Tyr Ser Val Glu Leu Tyr Thr Tyr Gly Cys Pro Arg Val
                165                 170                 175
Gly Asn Tyr Ala Leu Ala Glu His Ile Thr Ser Gln Gly Ser Gly Ala
            180                 185                 190
Asn Phe Pro Val Thr His Leu Asn Asp Ile Val Pro Arg Val Pro Pro
        195                 200                 205
Met Asp Phe Gly Phe Ser Gln Pro Ser Pro Glu Tyr Trp Ile Thr Ser
    210                 215                 220
Gly Thr Gly Ala Ser Val Thr Ala Ser Asp Ile Glu Leu Ile Glu Gly
225                 230                 235                 240
Ile Asn Ser Thr Ala Gly Asn Ala Gly Glu Ala Thr Val Asp Val Leu
                245                 250                 255
Ala His Leu Trp Tyr Phe Phe Ala Ile Ser Glu Cys Leu Leu
            260                 265                 270
```

<210> SEQ ID NO 15
<211> LENGTH: 269
<212> TYPE: PRT
<213> ORGANISM: Aspergillus oryzae

<400> SEQUENCE: 15

```
Asp Val Ser Ser Ser Leu Leu Asn Asn Leu Asp Leu Phe Ala Gln Tyr
 1               5                  10                  15
Ser Ala Ala Ala Tyr Cys Asp Glu Asn Leu Asn Ser Thr Gly Thr Lys
             20                  25                  30
Leu Thr Cys Ser Val Gly Asn Cys Pro Leu Val Glu Ala Ala Ser Thr
         35                  40                  45
Gln Ser Leu Asp Glu Phe Asn Glu Ser Ser Tyr Gly Asn Pro Ala
 50                  55                  60
Gly Tyr Leu Ala Ala Asp Glu Thr Asn Lys Leu Leu Val Leu Ser Phe
 65                  70                  75                  80
Arg Gly Ser Ala Asp Leu Ala Asn Trp Val Ala Asn Leu Asn Phe Gly
                 85                  90                  95
```

```
Leu Glu Asp Ala Ser Asp Leu Cys Ser Gly Cys Val His Ser Gly
            100                 105                 110

Phe Trp Lys Ala Trp Ser Glu Ile Ala Asp Thr Ile Thr Ser Lys Val
            115                 120                 125

Glu Ser Ala Leu Ser Asp His Ser Asp Tyr Ser Leu Val Leu Thr Gly
        130                 135                 140

His Ser Tyr Gly Ala Ala Leu Ala Ala Leu Ala Thr Ala Leu Arg
145                 150                 155                 160

Asn Ser Gly His Ser Val Glu Leu Tyr Asn Tyr Gly Gln Pro Arg Leu
                165                 170                 175

Gly Asn Glu Ala Leu Ala Thr Tyr Ile Thr Asp Gln Asn Lys Gly Gly
            180                 185                 190

Asn Tyr Arg Val Thr His Thr Asn Asp Ile Val Pro Lys Leu Pro Pro
            195                 200                 205

Thr Leu Leu Gly Tyr His His Phe Ser Pro Glu Tyr Tyr Ile Ser Ser
            210                 215                 220

Ala Asp Glu Ala Thr Val Thr Thr Thr Asp Val Thr Glu Val Thr Gly
225                 230                 235                 240

Ile Asp Ala Thr Gly Gly Asn Asp Gly Thr Asp Gly Thr Ser Ile Asp
                245                 250                 255

Ala His Arg Trp Tyr Phe Ile Tyr Ile Ser Glu Cys Ser
                260                 265

<210> SEQ ID NO 16
<211> LENGTH: 251
<212> TYPE: PRT
<213> ORGANISM: Landerina penisapora

<400> SEQUENCE: 16

Pro Gln Asp Ala Tyr Thr Ala Ser His Ala Asp Leu Val Lys Tyr Ala
1               5                   10                  15

Thr Tyr Ala Gly Leu Ala Tyr Gln Thr Thr Asp Ala Trp Pro Ala Ser
            20                  25                  30

Arg Thr Val Pro Lys Asp Thr Thr Leu Ile Ser Ser Phe Asp His Thr
            35                  40                  45

Leu Lys Gly Ser Ser Gly Tyr Ile Ala Phe Asn Glu Pro Cys Lys Glu
        50                  55                  60

Ile Ile Val Ala Tyr Arg Gly Thr Asp Ser Leu Ile Asp Trp Leu Thr
65                  70                  75                  80

Asn Leu Asn Phe Asp Lys Thr Ala Trp Pro Ala Asn Ile Ser Asn Ser
                85                  90                  95

Leu Val His Glu Gly Phe Leu Asn Ala Tyr Leu Val Ser Met Gln Gln
            100                 105                 110

Val Gln Glu Ala Val Asp Ser Leu Leu Ala Lys Cys Pro Asp Ala Thr
        115                 120                 125

Ile Ser Phe Thr Gly His Ser Leu Gly Gly Ala Leu Ala Cys Ile Ser
            130                 135                 140

Met Val Asp Thr Ala Gln Arg His Arg Gly Ile Lys Met Gln Met Phe
145                 150                 155                 160

Thr Tyr Gly Gln Pro Arg Thr Gly Asn Gln Ala Phe Ala Glu Tyr Val
                165                 170                 175

Glu Asn Leu Gly His Pro Val Phe Arg Val Tyr Arg His Asp Ile
            180                 185                 190

Val Pro Arg Met Pro Pro Met Asp Leu Gly Phe Gln His His Gly Gln
```

```
                195                 200                 205
Glu Val Trp Tyr Glu Gly Asp Glu Asn Ile Lys Phe Cys Lys Gly Glu
        210                 215                 220

Gly Glu Asn Leu Thr Cys Glu Leu Gly Val Pro Phe Ser Glu Leu Asn
225                 230                 235                 240

Ala Lys Asp His Ser Glu Tyr Pro Gly Met His
                245                 250
```

LIPOLYTIC ENZYME VARIANT WITH IMPROVED STABILITY AND POLYNUCLEOTIDES ENCODING SAME

CROSS-REFERENCE TO RELATED APPLICATIONS

This application claims priority or the benefit under 35 U.S.C. 119 of European application no. 08152164.3 filed Feb. 29, 2008 and U.S. provisional application No. 61/033,097 filed Mar. 3, 2008, the contents of which are fully incorporated herein by reference.

FIELD OF THE INVENTION

The present invention relates to lipolytic enzyme variants with improved in-detergent stability and to a method of preparing them. It particularly relates to lipolytic enzyme variants of the *Thermomyces lanuginosus* lipase.

SEQUENCE LISTING

The present application contains a computer-readable form of a sequence listing, which is fully incorporated herein by reference.

BACKGROUND OF THE INVENTION

It is known to use fungal lipolytic enzymes, e.g. the lipase from *Thermomyces lanuginosus* (synonym *Humicola lanuginosa*), for various industrial purposes, e.g. to improve the efficiency of detergents. Thus, a lipase derived from *Thermomyces lanuginosus* (synonym *Humicola lanuginosa*, EP 258 068 and EP 305 216) is sold for detergent use under the trade name Lipolase® (product of Novozymes A/S). WO 0060063 describes variants of the *T. lanuginosus* lipase with a particularly good first-wash performance in a detergent solution. In addition to the use of lipases as detergent enzymes to remove lipid or fatty stains from clothes and other textiles, they are also used as additives to dough for bread and other baked products, and in the elimination of pitch problems in pulp and paper production. In some applications, a lipolytic enzyme with improved thermostability is desirable (EP 374700, WO 9213130), whereas in other applications an in-detergent stability is desirable. WO 92/05249, WO 92/19726 and WO 97/07202 disclose variants of the *T. lanuginosus* (*H. lanuginosa*) lipase.

SUMMARY OF THE INVENTION

In a first aspect, the invention relates to a variant of a parent lipolytic enzyme, wherein the variant: (a) has an amino acid sequence which compared to the parent lipolytic enzyme comprises substitution of an amino acid residue corresponding to any of amino acids 27, 216, 227, 231, 233 and 256 of SEQ ID NO: 2; and (b) is more in-detergent stable than the parent lipolytic enzyme.

In further aspects, the invention relates to an isolated polynucleotide encoding the variant, a nucleic acid construct comprising the polynucleotide, a recombinant expression vector comprising the nucleic acid construct, and a transformed host cell comprising the nucleic acid construct or the recombinant expression vector.

In a further aspect, the invention relates to a method of preparing the lipolytic enzyme variant of any of claims 1-9 comprising the steps: (a) cultivating the transformed host cell comprising the nucleic acid construct or the recombinant expression vector comprising the polypeptide under conditions conductive for the production of the variant; and (b) recovering the variant.

In further aspects, the invention relates to use of the lipolytic enzyme variant in the hydrolysis of a carboxylic acid ester or in the hydrolysis, synthesis or interesterification of an ester.

In a further aspect, the invention relates to formulation comprising the lipolytic enzyme variant.

In a further aspect, the invention relates to use of the lipolytic enzyme variant for the manufacture of an in-detergent stable formulation.

BRIEF DESCRIPTION OF THE FIGURES

FIG. 1 shows the alignment of lipases.

SEQUENCE LISTINGS

SEQ ID NO: 1 shows the DNA sequence encoding lipase from *Thermomyces lanoginosus*.
SEQ ID NO: 2 shows the amino acid sequence of a lipase from *Thermomyces lanoginosus*.
SEQ ID NO: 3 shows the amino acid sequence of a lipase from *Absidia reflexa*.
SEQ ID NO: 4 shows the amino acid sequence of a lipase from *Absidia corymbifera*.
SEQ ID NO: 5 shows the amino acid sequence of a lipase from *Rhizomucor miehei*.
SEQ ID NO: 6 shows the amino acid sequence of a lipase from *Rhizopus oryzae*.
SEQ ID NO: 7 shows the amino acid sequence of a lipase from *Aspergillus niger*.
SEQ ID NO: 8 shows the amino acid sequence of a lipase from *Aspergillus tubingensis*.
SEQ ID NO: 9 shows the amino acid sequence of a lipase from *Fusarium oxysporrum*.
SEQ ID NO: 10 shows the amino acid sequence of a lipase from *Fusarium heterosporum*.
SEQ ID NO: 11 shows the amino acid sequence of a lipase from *Aspergillus oryzae*.
SEQ ID NO: 12 shows the amino acid sequence of a lipase from *Penicillium camemberti*.
SEQ ID NO: 13 shows the amino acid sequence of a lipase from *Aspergillus foetidus*.
SEQ ID NO: 14 shows the amino acid sequence of a lipase from *Aspergillus niger*.
SEQ ID NO: 15 shows the amino acid sequence of a lipase from *Aspergillus oryzae*.
SEQ ID NO: 16 shows the amino acid sequence of a lipase from *Landerina penisapora*.

DETAILED DESCRIPTION OF THE INVENTION

Nomenclature for Amino Acid Modifications

In describing lipase variants according to the invention, the following nomenclature is used for ease of reference:
Original amino acid(s):position(s):substituted amino acid(s)
According to this nomenclature, for instance the substitution of glutamic acid for glycine in position 195 is shown as G195E. A deletion of glycine in the same position is shown as G195*, and insertion of an additional amino acid residue such as lysine is shown as G195GK. Where a specific lipase contains a "deletion" in comparison with other lipases and an insertion is made in such a position this is indicated as *36D for insertion of an aspartic acid in position 36.

Multiple mutations are separated by pluses, i.e.: R170Y+ G195E, representing mutations in positions 170 and 195 substituting tyrosine and glutamic acid for arginine and glycine, respectively.

X231 indicates the amino acid in a parent lipolytic enzyme corresponding to position 231, when applying the described alignment procedure. X231R indicates that the amino acid is replaced with R. For SEQ ID NO: 2 X is T, and X231R thus indicates a substitution of T in position 231 with R. Where the amino acid in a position (e.g. 231) may be substituted by another amino acid selected from a group of amino acids, e.g. the group consisting of R and P and Y, this will be indicated by X231R/P/Y.

In all cases, the accepted IUPAC single letter or triple letter amino acid abbreviation is employed.

Identity: The term "identity" as used herein means the relatedness between two amino acid sequences or between two nucleotide sequences is described by the parameter "identity".

For purposes of the present invention, the alignment of two amino acid sequences is determined by using the Needle program from the EMBOSS package (http://emboss.org) version 2.8.0. The Needle program implements the global alignment algorithm described in Needleman, S. B. and Wunsch, C. D. (1970) J. Mol. Biol. 48, 443-453. The substitution matrix used is BLOSUM62, gap opening penalty is 10, and gap extension penalty is 0.5.

The degree of identity between an amino acid sequence of the present invention ("invention sequence"; e.g. amino acids 1 to 269 of SEQ ID NO: 2) and a different amino acid sequence ("foreign sequence") is calculated as the number of exact matches in an alignment of the two sequences, divided by the length of the "invention sequence" or the length of the "foreign sequence", whichever is the shortest. The result is expressed in percent identity.

An exact match occurs when the "invention sequence" and the "foreign sequence" have identical amino acid residues in the same positions of the overlap. The length of a sequence is the number of amino acid residues in the sequence (e.g. the length of SEQ ID NO: 2 are 269).

The above procedure may be used for calculation of identity as well as homology and for alignment. In the context of the present invention homology and alignment has been calculated as described below.

Homology and Alignment

For purposes of the present invention, the degree of homology may be suitably determined by means of computer programs known in the art, such as GAP provided in the GCG program package (Program Manual for the Wisconsin Package, Version 8, Aug. 1994, Genetics Computer Group, 575 Science Drive, Madison, Wis., USA 53711) (Needleman, S. B. and Wunsch, C. D., (1970), Journal of Molecular Biology, 48, 443-45), using GAP with the following settings for polypeptide sequence comparison: GAP creation penalty of 3.0 and GAP extension penalty of 0.1.

In the present invention, corresponding (or homologous) positions in the lipase sequences of *Absidia reflexa*, *Absidia corymbefera*, *Rhizmucor miehei*, *Rhizopus delemar*, *Aspergillus niger*, *Aspergillus tubigensis*, *Fusarium oxysporum*, *Fusarium heterosporum*, *Aspergillus oryzae*, *Penicilium camembertii*, *Aspergillus foetidus*, *Aspergillus niger*, *Thermomyces lanoginosus* (synonym: *Humicola lanuginose*) and *Landerina penisapora* are defined by the alignment shown in FIG. 1.

To find the homologous positions in lipase sequences not shown in the alignment, the sequence of interest is aligned to the sequences shown in FIG. 1. The new sequence is aligned to the present alignment in FIG. 1 by using the GAP alignment to the most homologous sequence found by the GAP program. GAP is provided in the GCG program package (Program Manual for the Wisconsin Package, Version 8, Aug. 1994, Genetics Computer Group, 575 Science Drive, Madison, Wis., USA 53711) (Needleman, S. B. and Wunsch, C. D., (1970), Journal of Molecular Biology, 48, 443-45). The following settings are used for polypeptide sequence comparison: GAP creation penalty of 3.0 and GAP extension penalty of 0.1.

Parent Lipases

Any suitable lipolytic enzyme may be used as a parent lipolytic enzyme also termed parent lipase. In some embodiments the lipolytic enzyme may be a fungal lipolytic enzyme.

The lipolytic enzyme may be a yeast lipolytic enzyme originating from genera such as a *Candida*, *Kluyveromyces*, *Pichia*, *Saccharomyces*, *Schizosaccharomyces*, or *Yarrowia*; or more preferably a filamentous fungal lipolytic enzyme originating from genera such as a *Acremonium*, *Aspergillus*, *Aureobasidium*, *Cryptococcus*, *Filobasidium*, *Fusarium*, *Humicola*, *Magnaporthe*, *Mucor*, *Myceliophthora*, *Neocallimastix*, *Neurospora*, *Paecilomyces*, *Penicillium*, *Piromyces*, *Schizophyllum*, *Talaromyces*, *Thermoascus*, *Thielavia*, *Tolypocladium*, *Thermomyces* or *Trichoderma*.

The lipolytic enzyme may furthermore be a *Saccharomyces carlsbergensis*, *Saccharomyces cerevisiae*, *Saccharomyces diastaticus*, *Saccharomyces douglasii*, *Saccharomyces kluyveri*, *Saccharomyces norbensis*, or *Saccharomyces oviform* is lipolytic enzyme.

Alternatively, the lipolytic enzyme is an *Aspergillus aculeatus*, *Aspergillus awamori*, *Aspergillus fumigatus*, *Aspergillus foetidus*, *Aspergillus japonicus*, *Aspergillus nidulans*, *Aspergillus niger*, *Aspergillus oryzae*, *Aspergillus turbigensis*, *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sporotrichioides*, *Fusarium sulphureum*, *Fusarium torulosum*, *Fusarium trichothecioides*, *Fusarium venenatum*, *Humicola insolens*, *Thermomyces lanoginosus* (synonym: *Humicola lanuginose*), *Mucor miehei*, *Myceliophthora thermophila*, *Neurospora crassa*, *Penicillium purpurogenum*, *Trichoderma harzianum*, *Trichoderma koningii*, *Trichoderma longibrachiatum*, *Trichoderma reesei*, or *Trichoderma viride* lipolytic enzyme.

In some embodiments the invention relates to a lipolytic enzyme variant which is a *Thermomyces* lipase or a *Thermomyces lanuginosus* lipase.

In some embodiments the invention relates to a lipolytic enzyme variant, wherein the variant is at least 50%, at least 60%, at least 70%, at least 80%, at least 85%, at least 90%, at least 91%, at least 92%, at least 93%, at least 94%, at least 95%, at least 96%, at least 97%, at least 98%, at least 99% or 100% identical to SEQ ID NO:2.

Alterations in Lipolytic Enzyme Variants having Improved In-Detergent Stability.

The positions referred to below are the positions of the amino acid residues in SEQ ID NO: 2. In the paragraph "Homology and alignment" a procedure of how to find the corresponding or homologous position of the amino acid residue in a different lipase is described.

The lipolytic enzyme variants, lipolytic variants, or in short variants, have according to the present invention surprisingly been found to be more in-detergent stable than the parent lipolytic enzyme. In-detergent stability is defined as the quality of retaining the lipolytic/lipase activity in the presence of detergent. The lipase activity may be fully or partly retained. Thus, variants of the invention show an improved ability to retain, either fully or partly, their lipase activity in the presence of detergent in comparison with parent lipases from which they are derived.

The term "lipase activity" as used herein means a carboxylic ester hydrolase activity which catalyses the hydrolysis of triacylglycerol under the formation of diacylglycerol and a carboxylate. For the purpose of the present invention, lipase activity is determined according to the following procedure: A substrate for lipase is prepared by emulsifying tributyrin (glycerin tributyrate) using gum Arabic as emulsifier. The hydrolysis of tributyrin at 30° C. at pH 7 or 9 is followed in a pH-stat titration experiment. One unit of lipase activity (1 LU) is defined as the amount of enzyme capable of releasing 1 micro mol of butyric acid per minute at 30° C., pH 7.

In some embodiments the variants according to the invention have been compared with a reference enzyme. The term "reference enzyme" or "reference lipase" as used herein means the mature part of SEQ ID NO: 2 with the substitutions T231R+N233R unless otherwise stated.

In some embodiments the invention relates to a variant of a parent lipolytic enzyme, wherein the variant: (a) has an amino acid sequence which compared to the parent lipolytic enzyme comprises substitution of an amino acid residue corresponding to any of amino acids 27, 216, 227, 231, 233 and 256 of SEQ ID NO: 2; and (b) is more in-detergent stable than the parent lipolytic enzyme.

In some embodiments the invention relates to a variant of a parent lipolytic enzyme, wherein the variant: (a) comprises the amino acid residues 231 and 233, and has an amino acid sequence which compared to the parent lipolytic enzyme comprises substitution of at least one amino acid residue corresponding to any of amino acids 27, 216, 227 and 256 of SEQ ID NO: 2; and (b) is more in-detergent stable than the parent lipolytic enzyme.

In some embodiments the invention relates to a variant of a parent lipolytic enzyme, wherein the variant having alterations of the amino acids at the positions 231+233 and one of: (a) 27; (b) 216; or (c) 256; optionally said variant furthermore comprises 227; which positions are corresponding to SEQ ID NO: 2.

In some embodiments the invention relates to a variant wherein the substitution of an amino acid residue is one of 27R, 216P, 227G, 231R, 233R or 256K of SEQ ID NO: 2.

In some embodiments the invention relates to a variant, wherein the substitution of an amino acid residue is one of D27R, S216P, L227G, T231R, N233R or P256K of SEQ ID NO: 2.

In some embodiments the invention relates to a variant, which variant comprises substitutions selected from the group consisting of: (a) T231R+N233R+P256K; (b) L227G+T231R+N233R; (c) L227G+T231R+N233R+P256K; (d) D27R+T231R+N233R; (e) D27R+L227G+T231R+N233R; and (f) S216P+T231R+N233R.

In some embodiments the invention relates to a variant, wherein the parent lipolytic enzyme is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO: 2.

In some embodiments the invention relates to a variant, wherein the parent lipolytic enzyme is a lipase produced by *Thermomyces lanuginosus* DSM 4109 and having the amino acid sequence of SEQ ID. NO: 2.

In some embodiments the invention relates to a variant, wherein the detergent is in a liquid detergent.

TABLE 1

Alterations that may be comprised in the lipolytic enzyme variants

| Variant | Mutations in SEQ ID NO: 2 |
|---|---|
| 1 | T231R + N233R + P256K |
| 2 | L227G + T231R + N233R |
| 3 | L227G + T231R + N233R + P256K |
| 4 | D27R + T231R + N233R |
| 5 | D27R + L227G + T231R + N233R |
| 6 | S216P + T231R + N233R |

In some embodiments the invention relates to a formulation comprising the lipolytic enzyme variant.

In some embodiments the invention relates to a formulation, wherein said formulation may be a liquid formulation. Polynucleotides, Expression Vector, Host Cell, Production of Lipolytic Enzyme Variants.

In some embodiments the invention relates to an isolated polynucleotide encoding the lipolytic enzyme variants. Polynucleotides may hybridize under very low stringency conditions, preferably low stringency conditions, more preferably medium stringency conditions, more preferably medium-high stringency conditions, even more preferably high stringency conditions, and most preferably very high stringency conditions with (i) nucleotides 178 to 660 of SEQ ID NO: 1, (ii) the cDNA sequence contained in nucleotides 178 to 660 of SEQ ID NO: 1, (iii) a subsequence of (i) or (ii), or (iv) a complementary strand of (i), (ii), or (iii) (J. Sambrook, E. F. Fritsch, and T. Maniatis, 1989, Molecular Cloning, A Laboratory Manual, 2d edition, Cold Spring Harbor, N.Y.). A subsequence of SEQ ID NO: 1 contains at least 100 contiguous nucleotides or preferably at least 200 contiguous nucleotides. Moreover, the subsequence may encode a polypeptide fragment which has lipase activity.

For long probes of at least 100 nucleotides in length, very low to very high stringency conditions are defined as prehybridization and hybridization at 42° C. in 5×SSPE, 0.3% SDS, 200 ug/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally.

For long probes of at least 100 nucleotides in length, the carrier material is finally washed three times each for 15 minutes using 2×SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency).

In some embodiments the invention relates to a nucleic acid construct comprising the polynucleotide operationally linked to at least one control sequence that directs the production of the lipolytic enzyme variant in an expression host.

In some embodiments the invention relates to a recombinant expression vector comprising the nucleic acid construct.

In some embodiments the invention relates to a transformed host cell comprising the nucleic acid construct or the recombinant expression vector.

The isolated polynucleotide encoding the lipolytic enzyme variant, the nucleic acid construct comprising the polynucleotide, the recombinant expression vector comprising the nucleic acid construct, and the transformed host cell comprising the nucleic acid construct or the recombinant expression vector may all be obtained by methods known in the art.

Procedure for Obtaining In-Detergent Stable Lipolytic Enzyme Variants

Variants of lipolytic enzymes may be obtained by methods known in the art, such as sitedirected mutagenesis, random mutagenesis or localized mutagenesis, e.g. as described in WO 9522615 or WO 0032758. In-detergent stable variants of a given parent lipolytic enzyme may be obtained by the following standard procedure:

Mutagenesis (error-prone, doped oligo, spiked oligo)
Primary Screening
Identification of more in-detergent stable mutants
Maintenance (glycerol culture, LB-Amp plates, Mini-Prep)
Streaking out on another assay plate—secondary screening (1 degree higher then primary screening)
DNA Sequencing
Transformation into a host cell, such as e.g. *Aspergillus*
Cultivation in 100 ml scale, purification, DSC In some embodiments the invention relates to a method of preparing the lipolytic enzyme variant comprising the steps: (a) cultivating the transformed host cell comprising the nucleic acid construct or the recombinant expression vector comprising the nucleotide acid construct under conditions conductive for the production of the lipolytic enzyme variant; and (b) recovering the lipolytic enzyme variant. The method may be practiced according to principles known in the art.

In some embodiments the invention relates to a method of producing the variant comprising the steps: (a) selecting a parent lipolytic enzyme; (b) in the parent lipolytic enzyme substituting at least one amino acid residue corresponding to any of 27, 216, 227, 231, 233 and 256 of SEQ ID NO: 2; (c) optionally, altering one or more amino acids other than those mentioned in (b); (d) preparing the variant resulting from steps (a)-(c); (e) testing the in-detergent stability of the variant; (f) selecting a variant having an increased in-detergent stability; and (g) producing the selected variant.

Uses

The variants according to the invention may be used analogous to the parent lipolytic enzymes, and for some purposes the variants may be preferred due to their improved in-detergent stability. Thus, in some embodiments the invention relates to use of the variant in the hydrolysis of a carboxylic acid ester, or in the hydrolysis, synthesis or interesterification of an ester.

In some embodiments the invention relates to use of the variant for the manufacture of an in-detergent stable formulation.

EXAMPLES

The present invention is further described by the following examples which should not be construed as limiting the scope of the invention.

Chemicals used as buffers and substrates were commercial products of at least reagent grade.

Example 1

Expression of Lipase Variants

A plasmid containing the gene encoding the lipolytic enzyme variant is constructed and transformed into a suitable host cell using standard methods of the art.

Example 2

Production of Lipase Variants

Fermentation is carried out as a fed-batch fermentation using a constant medium temperature of 34° C. and a start volume of 1.2 liter. The initial pH of the medium is set to 6.5. Once the pH has increased to 7.0 this value is maintained through addition of 10% $H_3PO_4$. The level of dissolved oxygen in the medium is controlled by varying the agitation rate and using a fixed aeration rate of 1.0 liter air per liter medium per minute. The feed addition rate is maintained at a constant level during the entire fed-batch phase.

The batch medium contains maltose syrup as carbon source, urea and yeast extract as nitrogen source and a mixture of trace metals and salts. The feed added continuously during the fed-batch phase contains maltose syrup as carbon source whereas yeast extract and urea is added in order to assure a sufficient supply of nitrogen.

Purification of the lipolytic enzyme variant may be done by use of standard methods known in the art, e.g. by filtering the fermentation supernatant and subsequent hydrophobic chromatography and ion exchange chromatography, e.g. as described in EP 0 851 913 EP, Example 3.

Example 3

In-Detergent Stability of Lipolytic Enzyme Variants

The following lipolytic enzyme variants were tested for stability in detergent and compared to the reference lipolytic enzyme SEQ ID NO: 2.

TABLE 2

The tested lipolytic enzyme variants.

| Variant | Mutations in SEQ ID NO: 2 | Specific activity LU/A280 |
|---|---|---|
| Ref | — | 4760 |
| 1 | T231R + N233R + P256K | 963 |
| 2 | L227G + T231R + N233R | 5000 |
| 3 | L227G + T231R + N233R + P256K | 2674 |
| 4 | D27R + T231R + N233R | 3199 |
| 5 | D27R + L227G + T231R + N233R | 5020 |
| 6 | S216P + T231R + N233R | 3323 |

The lipolytic enzyme variants and the reference were dosed to a concentration of 0.065 mg enzyme protein per gram commercial detergent.

TABLE 3

Composition of the detergent.

| INGREDIENT | Origin | % wt. |
|---|---|---|
| Sodium alkyl ether sulphate | Steol 25-2S.70, Stepan Deutschland | 12.0 |
| LAS | Surfac SDBS80, Surfachem | 7.0 |
| Soap Tallow/Coconut 80/20 | Linds Fabrikker | 3.2 |
| 23-9 Alcohol ethoxylate | Neodol 23-9, Shell Chemical | 2.4 |
| Alkyl dimethylamine oxide | Empigen OB, Huntsman | 2.0 |
| Citric acid (sodium) | Merck | 2.8 |
| Sodium hydroxide 10N | Bie & Berntsen | 1.6 |
| Glycerine | Optim Glycerine 99.7% USP/EP, Dow Chemical | 2.3 |

TABLE 3-continued

Composition of the detergent.

| INGREDIENT | Origin | % wt. |
|---|---|---|
| Monoethanolamine | Huntsman | 2.7 |
| MPG | Proylene Glycol Industrial, Dow Chemical | 4.7 |
| Water | | 59.3 |

Samples comprising detergent and lipolytic enzyme variants or a reference enzyme were dissolved in tris(hydroxymethyl)aminomethan (TRIS) buffer at pH=7.7 and stored at −18° C. and 35° C. for 2 and 4 weeks respectively. The residual enzymatic activity was calculated as the lipase activity after incubation at 35° C. divided by the lipase activity of the samples stored at −18° C. The stability data are shown in Table 4 below. All six lipolytic enzyme variants demonstrated improved in-detergent stability, compared to the reference lipase.

The lipase activity was measured by monitoring the hydrolysis of the substrate p-Nitrophenyl-Valerate (pNp-Val) to generate the products valerate and pNp. Detection wavelength=405 nm; pH=7.7; and temperature=37° C. All lipases having esterase activity at this pH can be analyzed with this method.

TABLE 4

Residual lipolytic activity after storage. Data shown as an average of triplicates.

| | Variant: | | | | | | |
|---|---|---|---|---|---|---|---|
| | Ref. | 1 | 2 | 3 | 4 | 5 | 6 |
| −18° C. | 0.238 | 0.272 | 0.255 | 0.266 | 0.238 | 0.248 | 0.175 |
| | 0.242 | 0.285 | 0.239 | 0.260 | 0.216 | 0.260 | 0.188 |
| | 0.237 | 0.299 | 0.236 | 0.273 | 0.216 | 0.256 | 0.184 |
| Average −18° C. | 0.239 | 0.285 | 0.243 | 0.267 | 0.223 | 0.255 | 0.182 |
| 2 weeks 35° C. | 0.191 | 0.254 | 0.193 | 0.215 | 0.190 | 0.236 | 0.173 |
| | 0.170 | 0.249 | 0.196 | 0.224 | 0.202 | 0.239 | 0.169 |
| | 0.170 | 0.250 | 0.194 | 0.233 | 0.200 | 0.239 | 0.167 |
| Average 2 w | 0.177 | 0.251 | 0.195 | 0.224 | 0.197 | 0.238 | 0.170 |
| 4 weeks 35° C. | 0.133 | 0.217 | 0.156 | 0.203 | 0.175 | 0.221 | 0.165 |
| | 0.135 | 0.211 | 0.155 | 0.204 | 0.176 | 0.218 | 0.158 |
| | 0.134 | 0.216 | 0.154 | 0.200 | 0.180 | 0.218 | 0.156 |
| Average 4 w | 0.134 | 0.215 | 0.155 | 0.203 | 0.177 | 0.219 | 0.160 |
| % Residual activity 2 w | 74 | 88 | 80 | 84 | 88 | 93 | 93 |
| % Residual activity 4 w | 56 | 75 | 64 | 76 | 79 | 86 | 88 |

The invention claimed is:

1. An isolated variant of a parent lipolytic enzyme of SEQ ID NO: 2, wherein the variant:
   has an amino acid sequence which compared to the parent lipolytic enzyme consists of substitution of the amino acid residues selected from the group consisting of:
   i. T231R+N233R+P256K;
   ii. L227G+T231R+N233R;
   iii. D27R+T231R+N233R;
   iv. D27R+L227G+T231R+N233R; and
   v. S216P+T231R+N233R
   of SEQ ID NO: 2 and is more in-detergent stable than the parent lipolytic enzyme.

2. The variant of claim 1, wherein the detergent is a liquid detergent.

3. A formulation comprising the variant of claim 1.

4. The formulation of claim 3, wherein said formulation is a liquid formulation.

5. The variant of claim 1, consisting of the substitutions T231R+N233R+P256K.

6. The variant of claim 1, consisting of the substitutions L227G+T231R+N233R.

7. The variant of claim 1, consisting of the substitutions D27R+T231R+N233R.

8. The variant of claim 1, consisting of the substitutions D27R+L227G+T231R+N233R.

9. The variant of claim 1, consisting of the substitutions S216P+T231R+N233R.

* * * * *